(12) United States Patent
Pavcnik et al.

(10) Patent No.: US 7,686,842 B2
(45) Date of Patent: Mar. 30, 2010

(54) ENDOVASCULAR STENT GRAFT

(75) Inventors: Dusan Pavcnik, Portland, OR (US);
Josef Rösch, Portland, OR (US);
Frederick S. Keller, Portland, OR (US)

(73) Assignee: Oregon Health Sciences University, Portland, OR (US)

(*) Notice: Subject to any disclaimer, the term of this patent is extended or adjusted under 35 U.S.C. 154(b) by 0 days.

(21) Appl. No.: 09/849,044

(22) Filed: May 4, 2001

(65) Prior Publication Data

US 2001/0041928 A1  Nov. 15, 2001

Related U.S. Application Data

(60) Provisional application No. 60/201,806, filed on May 4, 2000.

(51) Int. Cl.
*A61F 2/06* (2006.01)
(52) U.S. Cl. .................................. 623/1.13
(58) Field of Classification Search ............... 623/1.13, 623/1.25, 1.36, 1.42–1.54, 1.11, 1.15, 1.35, 623/1.23; 606/198, 197, 195, 194
See application file for complete search history.

(56) References Cited

U.S. PATENT DOCUMENTS

| | | | | |
|---|---|---|---|---|
| 4,130,904 A | * | 12/1978 | Whalen ...................... 623/1.44 |
| 5,035,706 A | * | 7/1991 | Giantureo et al. ............ 606/198 |
| 5,123,917 A | * | 6/1992 | Lee .......................... 623/22.26 |
| 5,282,824 A | * | 2/1994 | Gianturco .................. 623/1.13 |
| 5,405,377 A | * | 4/1995 | Cragg ......................... 623/1.2 |
| 5,507,767 A | * | 4/1996 | Maeda et al. ................. 623/1.2 |
| 5,507,771 A | | 4/1996 | Gianturco |
| 5,522,881 A | * | 6/1996 | Lentz ......................... 623/1.13 |
| 5,665,115 A | * | 9/1997 | Cragg ........................ 623/1.13 |
| 5,693,085 A | * | 12/1997 | Buirge et al. ................ 623/1.13 |
| 5,693,088 A | * | 12/1997 | Lazarus ...................... 623/1.35 |
| 5,720,776 A | * | 2/1998 | Chuter et al. ............... 623/1.36 |
| 5,733,337 A | | 3/1998 | Carr, Jr. et al. |
| 5,735,892 A | * | 4/1998 | Myers et al. ................ 623/1.13 |

(Continued)

FOREIGN PATENT DOCUMENTS

WO 9724081 7/1997

(Continued)

OTHER PUBLICATIONS

PCT Application No. PCT/US01/03095, filed Jan. 21, 2001; Stent Valves and Uses of Same.

(Continued)

*Primary Examiner*—Alvin Stewart
(74) *Attorney, Agent, or Firm*—Woodward, Emhardt, Moriarty, McNett & Henry LLP

(57) ABSTRACT

A stent graft (10) with a stent frame (12) having a plurality of stents (16) connected together with monofilament line (22). A covering (14) of collagen having an extracellular matrix (ECM), such as small intestine submucosa (SIS), is disposed through the inside and over the outside of the stent frame. The covering (14) is affixed to the stent frame (12) such as by being sutured onto the stent frame at the ends of the stent frame and also at the connections of the stent bodies, such as at eyelets (24).

11 Claims, 2 Drawing Sheets

U.S. PATENT DOCUMENTS

| | | | |
|---|---|---|---|
| 5,746,766 A * | 5/1998 | Edoga .................... 623/1.2 |
| 5,922,028 A | 7/1999 | Plouhar et al. |
| 5,955,110 A | 9/1999 | Patel et al. |
| 5,980,565 A | 11/1999 | Jayaraman |
| 5,990,379 A * | 11/1999 | Gregory .................... 128/898 |
| 6,010,529 A * | 1/2000 | Herweck et al. ......... 623/23.69 |
| 6,090,128 A * | 7/2000 | Douglas .................... 623/1.11 |
| 6,126,686 A | 10/2000 | Badylak et al. |
| 6,165,212 A * | 12/2000 | Dereume et al. ........... 623/1.13 |
| 6,197,049 B1 * | 3/2001 | Shaolian et al. ........... 623/1.35 |
| 6,206,931 B1 | 3/2001 | Cook et al. |
| 6,270,523 B1 * | 8/2001 | Herweck et al. ........... 623/1.13 |
| 6,287,337 B1 * | 9/2001 | Martakos et al. ........... 623/1.39 |
| 6,296,661 B1 * | 10/2001 | Davila et al. ............... 623/1.13 |
| 6,309,343 B1 * | 10/2001 | Lentz et al. .................... 600/36 |
| 6,383,214 B1 * | 5/2002 | Banas et al. ................ 623/1.14 |
| 6,475,232 B1 * | 11/2002 | Babbs et al. ................ 623/1.13 |
| 6,613,082 B2 * | 9/2003 | Yang .......................... 623/1.42 |
| 6,752,826 B2 * | 6/2004 | Holloway et al. ........... 623/1.13 |
| 6,951,572 B1 * | 10/2005 | Douglas .................... 623/1.35 |
| 7,083,640 B2 * | 8/2006 | Lombardi et al. ........... 623/1.18 |
| 7,186,263 B2 * | 3/2007 | Golds et al. ................. 623/1.13 |
| 7,354,449 B2 * | 4/2008 | Goodwin et al. ........... 623/1.13 |
| 7,491,226 B2 * | 2/2009 | Palmaz et al. .............. 623/1.13 |
| 7,550,003 B2 * | 6/2009 | Sogard et al. ............... 623/1.13 |

FOREIGN PATENT DOCUMENTS

| | | |
|---|---|---|
| WO | 9825544 | 6/1998 |
| WO | 9844870 | 10/1998 |
| WO | 9962431 | 12/1999 |
| WO | 0119285 | 3/2001 |

OTHER PUBLICATIONS

Katsuyuki Yamada et al; Endoluminal Treatment of Ruptured Abdominal Aortic Aneurysm with Small Intestinal Submucosa Sandwich Endografts: A Pilot Study in Sheep; 2001; CardioVascular and Interventional Radiology; Springer-Verlag, New York, Inc.

Written Opinion issued by European Patent Office on Jul. 10, 2002 on International Application No. PCT/US01/14495.

* cited by examiner

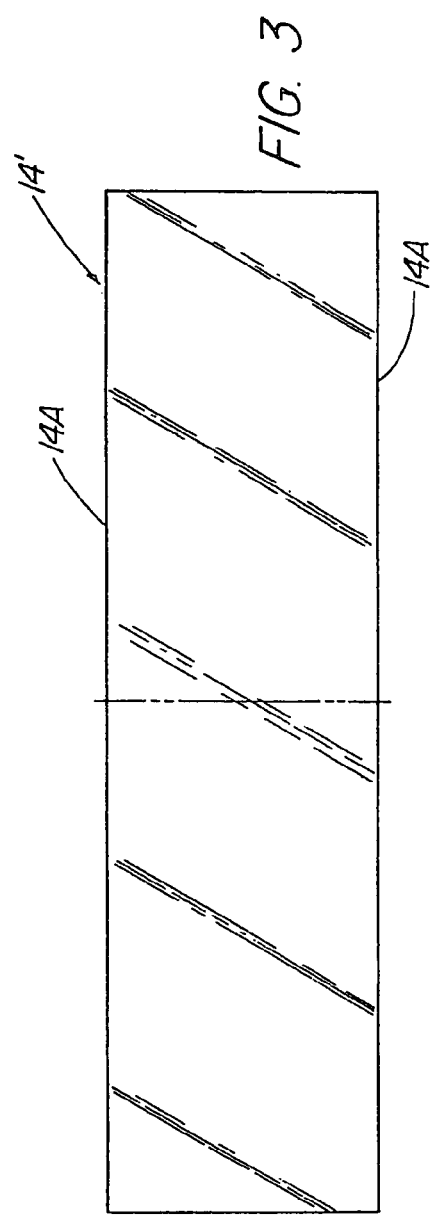
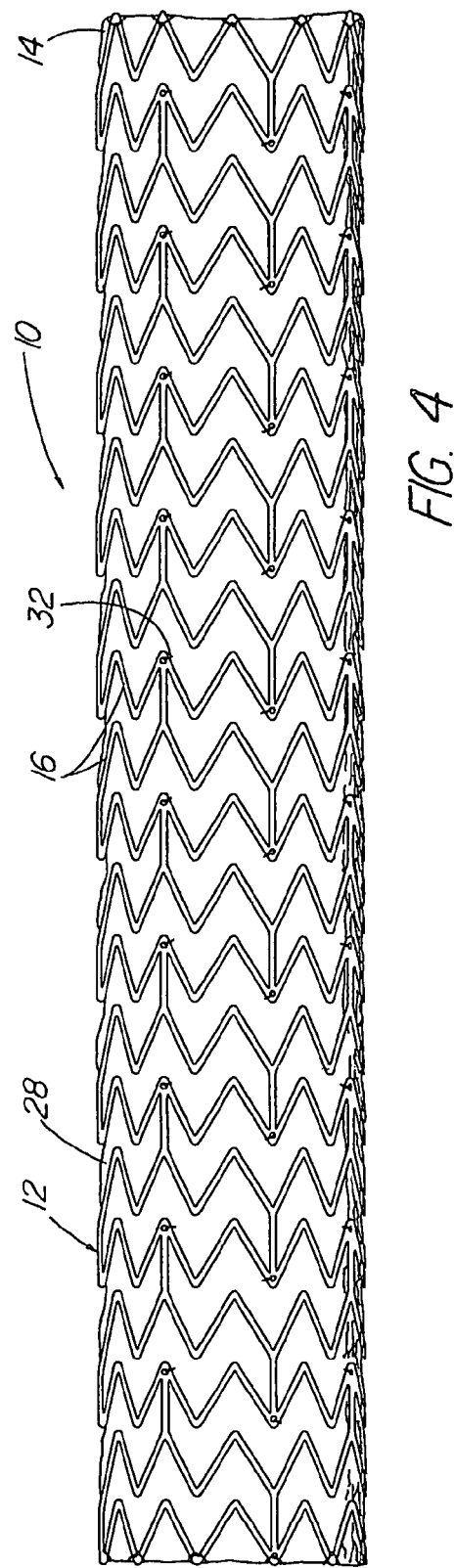

US 7,686,842 B2

ENDOVASCULAR STENT GRAFT

RELATED APPLICATION INFORMATION

This application claims priority from U.S. Provisional Application No. 60/201,806 filed May 4, 2000.

FIELD OF THE INVENTION

The present invention relates to medical devices and more particularly to stent grafts for vascular placement.

BACKGROUND OF THE INVENTION

Endoluminal exclusion of abdominal aortic aneurysms (AAA) by transluminal implantation of stent grafts has in selected cases become an attractive alternative to open surgical aneurysmal repair. It has been done on an elective basis after detailed preoperative visualization and measurements are made of the aneurysmal and adjacent arterial anatomy. Recent developments and a greater variety of new stent graft systems has enabled endoluminal exclusion to be extended to patients with ruptured AAA and to perform it on emergency basis. The stent graft systems for both elective and emergency AAA exclusions have been constructed with conventional surgical synthetic materials DACRON® or polytetrafluoroethylene (PTFE) supported by metallic expandable stents.

Conventionally, stent grafts that are emplaced within the vascular networks include one or more stents affixed to graft material. The stent grafts are secured at a treatment site by endovascular insertion utilizing introducers and catheters, whereafter they are enlarged radially and remain in place by self-attachment to the vessel wall. In particular, stent grafts are known for use in treating descending thoracic and abdominal aortic aneurysms where the stent graft at one end defines a single lumen for placement within the aorta and at the other end is bifurcated to define two lumens, for extending into the branch arteries.

One example of such a stent graft is disclosed in PCT Publication No. WO 98/53761 in which the stent graft includes a sleeve or tube of biocompatible graft material (such as DACRON® or polytetrafluoroethylene) defining a lumen, and further includes several stents secured therealong, with the stent graft spanning the aneurysm extending along the aorta proximally from the two iliac arteries; the reference also discloses the manner of deploying the stent graft in the patient utilizing an introducer assembly. The graft material-covered portion of the single-lumen proximal end of the stent graft bears against the wall of the aorta above the aneurysm to seal the aneurysm at a location that is spaced distally of (farther from the heart) the entrances to the renal arteries. Thin wire struts of a proximal stent extension traverse the renal artery entrances without occluding them, since no graft material is utilized along the proximal stent while securing the stent graft in position within the aorta when the stent self-expands. An extension is affixed to one of the legs of the stent graft to extend along a respective iliac artery and, optionally, extensions may be affixed to both legs. Another known stent graft is the ZENITH™ AAA stent graft sold by William A. Cook Pty. Ltd., Brisbane, Queensland, AU.

SUMMARY OF THE INVENTION

The stent frame of the present invention comprises at least one stent, and preferably a plurality of stents connected together such as with monofilament line to define a stent frame. Accompanying the stent or stent frame is a sleeve or tube of a naturally occurring biomaterial, such as collagen, which is highly desirable, particularly a specially derived collagen material known as an extracellular matrix (ECM), such as small intestinal submucosa (SIS). A layer of the small intestine submucosa (SIS) is disposed along at least the inside surface and preferably also along the outside surface of the stent frame. The SIS tube is affixed to the stent frame at the ends of the stent frame and preferably also at the connections of the stent bodies, such as by sutures, and additional sutures may optionally also be placed in the middle of every leg of each stent.

Preferably, the tube of SIS is an intestinal wall segment that is integral circumferentially and of appropriate diameter, and that initially is twice as long as the stent frame so that it is first inserted within and along the frame when the stent frame is in its fully expanded state, and the tube then is everted to be folded back from one end of the frame and along the outside of the frame, defining a stent graft with two layers of SIS material for strength, sutured to the stent frame along its inner and outer surfaces. In another aspect, the tube may be initially a sheet (or several sheets) of SIS material that is sewn into a tubular form and then assembled to the stent frame.

The objective of the present invention is to provide SIS sandwich stent grafts for treatment of acute AAA rupture and short-term reaction of native aorta to their placement.

BRIEF DESCRIPTION OF THE DRAWING

An embodiment of the present invention will now be described by way of example with reference to the accompanying drawings, in which:

FIG. 3 illustrates a sheet of SIS material prior to being formed into a sleeve shape; and FIG. 4 illustrates an inside layer of SIS within a stent frame.

DETAILED DESCRIPTION

Figure 1:
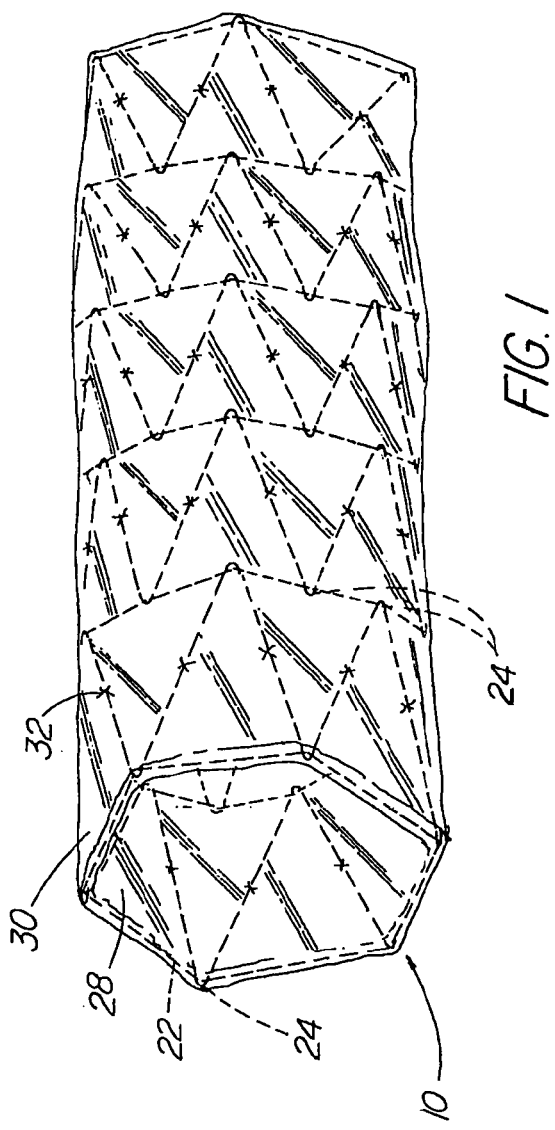
FIG. 1 is an elevation view of the stent graft of the present invention.
Figure 2:
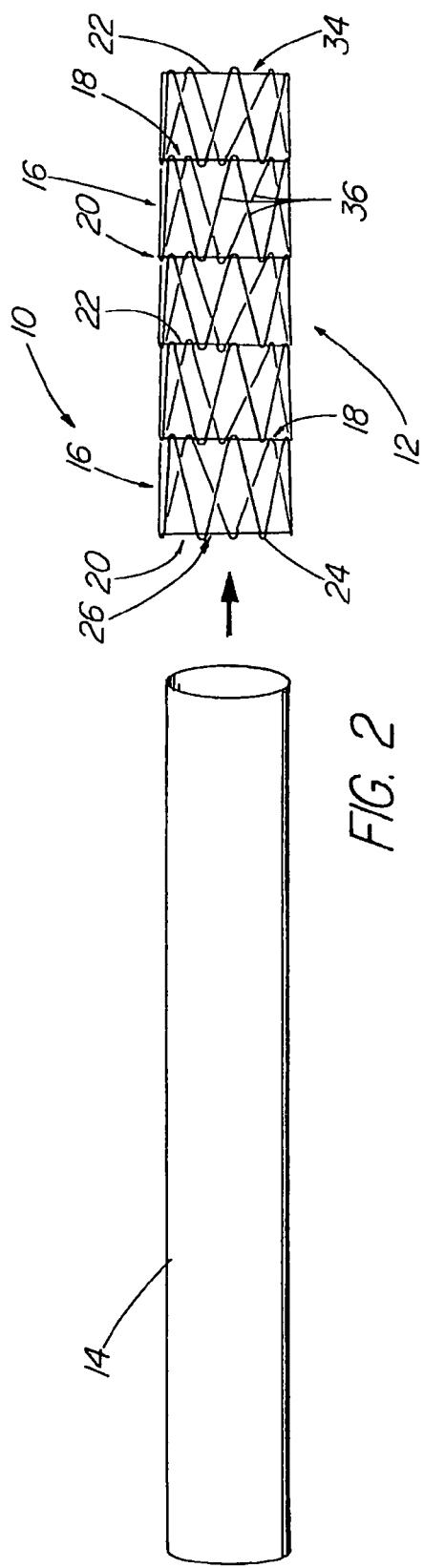
FIG. 2 illustrates the stent frame and the SIS sleeve.

The figures show a stent graft 10 (FIG. 1) that is comprised of a stent frame 12 (FIG. 2) and a covering 14 (FIGS. 2 and 3) having a sleeve or tube shape. Stent frame 12 is comprised of one or more stents 16 having first and second opposite ends 18,20, with adjacent ones of stents 16 being secured together by a monofilament 22 at adjacent first and second stent ends 18,20. Preferably the stents are of the type having eyes, loops or eyelets 24 that locate the monofilament at a fixed position axially therealong. Stents 16 are of the type that are self-expandable or optionally balloon-expandable so that they may be reduced in diameter for delivery through a catheter along the vasculature of the patient to the treatment site, such as in the aorta, whereupon they expand or are expanded to resume a larger diameter and press against the vessel wall and become anchored in position. Such stents may be of stainless steel, such as in wire form, or may be of a superelastic material such as nitinol; the stent frame may also be of cannula such as is disclosed in PCT Publication No. WO US98/19990.

In accordance with the present invention, covering 14 is of an ECM, such as small intestine submucosa (SIS), which material and its preparation and use is described in greater detail in U.S. Pat. No. 6,206,931 B1. SIS is a relatively acellular, collagen-based biomaterial obtained from swine small intestines which provides a framework for cells that after emplacement within a patient, becomes remodeled by host tissue and degrades and reabsorbs over time. It is resistant to infection and does not cause an adverse immunologic reaction. The SIS material is of the type sold as OASIS® wound dressing and as SURGISIS® surgical mesh (Cook Biotech, Inc., West Lafayette, Ind.). SIS material has displayed excellent physical and mechanical properties when surgically used as aortic, carotid and superior vena cava grafts; it becomes replaced by adjacent host tissue and becomes identical to the native vessel.

Besides SIS, examples of ECM's include pericardium, stomach submucosa, liver basement membrane, urinary bladder submucosa, tissue mucosa, and dura mater. SIS is particularly useful, and can be made in the fashion described in Badylak et al., U.S. Pat. No. 4,902,508; also see Intestinal Collagen Layer described in U.S. Pat. No. 5,733,337 to Carr and in 17 Nature Biotechnology 1083 (November 1999); and see Cook et al., WIPO Publication WO 98/22158, dated May 28, 1998. Irrespective of the origin of the material (synthetic versus naturally occurring), the material can be made thicker by making multilaminate constructs, for example SIS constructs as described in U.S. Pat. Nos. 5,968,096; 5,955,110; 5,885,619; and 5,711,969. Animal data show that the SIS used in venous valves can be replaced by native tissue in as little as a month's time. Additionally Elastin or Elastin Like Polypeptides (ELPs) and the like offer potential as a material to fabricate the covering to form a device with exceptional biocompatibility.

In the present invention, the sleeve or tube shape 14 has a wall thickness about 0.1 mm thick and is of a diameter selected to complement the vessel diameter, and the diameter of the stent frame is likewise so selected. The tube 14 may be either the type that remains integral circumferentially during processing after removal from the small intestine (FIG. 2), or may be processed initially into a flat tissue 14' (FIG. 3) having opposite lateral edges 14A which are then connected together along a seam such as by suturing to define a sleeve shape; the sleeve may also be several such tissues sewn together. In FIG. 4, a single layer of SIS material covering 14 is shown as an inner layer 28 within the stent frame 12, with running sutures stitching the covering to the stent eyelets at every second row of the small Z-shaped strut pattern of the stents 16, such as with synthetic absorbable surgical suture 32 of 7-0 polyglyconate. An outer layer of SIS material may similarly be secured to the stent frame.

The tube 14 is selected to have an axially length as long as the length of the stent frame, and preferably twice such length, so that the tube may be secured to the stent frame along the inside surface of the stent frame and also along the outside surface thereof. The tube 14 is initially inserted through the lumen of stent frame 12 to extend beyond proximal end 26. Tube 14 is then everted to be drawn back over proximal end 26 and along the outside surface of stent frame 12, thus forming a "sandwich" having two SIS material layers 28,30 that extend along both the inside and outside surfaces of the stent frame, respectively. It is preferable that the stent graft end at which the sleeve is folded over, be the proximal end, since the fold will prevent blood flow between the layers.

The two layers of SIS material 28,30 are preferably both secured to the stent frame by suturing. Using a conventional suture 32 of a biocompatible filament such as 7-0 polypropylene (PROLENE®, Ethicon Inc., Somerville, N.J.), the SIS material layers are secured to the stent frame, at least at both the proximal and distal ends 26,34 of the stent frame, and preferably at the first and second ends 18,20 of each stent 16 of the stent frame. Optionally, the SIS covering may be also sutured to the midpoints of each strut 36 of each stent 16. One such stent frame is disclosed in U.S. Pat. No. 5,282,824 in which each stent of the frame comprises a zig-zag arrangement of struts disposed in a circumferential arrangement, the ends of each strut being joined to the ends of adjacent struts at eyes or eyelets, and the first and second ends of the stent being a circular array of such eyelets. It is preferable that the stent frame be such as to provide eyes, loops, eyelets or other similar formation to secure the suture connecting the covering to the stent frame thereat, from movement along the struts of the stents. Suturing is preferred over other forms of connecting the sleeve to the stent frame, since no other materials are thus used that could adversely interact or affect the SIS material, or other methods are used such as heat or photoactivating radiation commonly used to cure bonding materials.

Suturing of the SIS covering at stent eyelets 24 assures that the suture 32 will remain fixed in position axially with respect to the stent frame. The suturing procedure is conducted with the stents of the stent frame at their fully expanded diameter, corresponding generally to the diameter of the tube 14, so that upon reexpansion during deployment at the treatment site in the aorta, the covering will only be minimally stressed in the circumferential direction, thus only minimally stressing the perforations through the tissue forming during the suturing procedure. Axial stability of the stent frame assures that the tube 14 will be at most only minimally stressed in the axial direction upon deployment at the treatment site. Preferably, the suture joins the covering to the stent frame at those locations of the stent frame that assure that the suture is fixed in position against movement along the struts of the stent.

SIS sandwich stent graft placement excludes the aneurysm and the rupture, when present. The SIS sandwich stent graft effectively excludes AAA and aortic rupture and is rapidly incorporated in the aortic wall. Gross and histologic studies reveal incorporation of the stent grafts into the aortic wall with replacement of SIS by dense neointima which is completely endothelialized in areas where the stent graft is in direct contact with the aortic wall.

Examples of the SIS sandwich stent grafts were hand-made in the research laboratory of the Oregon Health Science University. The stent frame consisted of five Gianturco-Rösch Z® stents (Cook Incorporated, Bloomington, Ind.) constructed from 0.012" stainless steel wire and connected together with 5/0-monofilament nylon line. Their diameter was 15 mm and each was 1.5 cm long. The stent combination was thus 7.5 cm long. Wet SIS sheets (Cook Biotech Inc., West Lafayette, Ind.) 0.1 mm thick were sewn in to a sleeve or tube shape which was placed through the inside and over the outside of the stent frame. The SIS tube was connected to the stent frame on the outside at the connection of the first and second stent bodies using 7-0 polypropylene (PROLENE®, Ethicon Inc., Somerville, N.J.). Interrupted sutures were also placed at the other stent bodies' connections and in the middle of every leg of each stent. The completed SIS sandwich stent graft measured 14 mm in diameter and was 7.5 cm long. The SIS sandwich stent grafts were soaked in antibiotic solution (CEFOTAN®, Lenea Pharmaceuticals, Wilmington, Del.) for at least 24 hours before placement.

Vascular sheaths were introduced into the right carotid and right femoral arteries. A 40 cm long 12-F sheath was introduced into the carotid artery and advanced into the descending aorta, for introduction of an occlusion balloon catheter. The occlusion balloon was advanced into the upper abdominal aorta and was used to control bleeding from aortic rupture. An 8-F sheath was introduced into the femoral artery and advanced into the abdominal aorta. After intraaortic administration of 3000-IU heparin, a 6-F pigtail catheter was advanced in the abdominal aorta and an aortography was performed. The diameter of the infrarenal aorta was measured with a calibration guidewire introduced through the occlusion balloon.

The SIS sandwich stent graft was loaded in the distal tip of an 11-F sheath and delivered to the AAA through the femoral 12.5-F sheath. The stent graft was held in position with a pusher to cover the entire AAA while the 11-F sheath was withdrawn. Aortography was then repeated with a multiple side hole pigtail catheter from the carotid sheath. Full expansion of the stent graft was assured by dilation with a 15 mm-diameter balloon catheter.

The SIS sandwich stent grafts were placed into the distal aorta excluding the aneurysm and the aortic rupture. Being preloaded, stent placement was expeditious and lasted no more than 2 to 3 minutes. Pressure measurements through the stent grafts did not show any gradient. Immediate follow-up aortograms showed excellent aortic patency, exclusion of the aortic ruptures and no evidence of leaks around the stent grafts. Abdominal aortograms showed excellent patency of stent grafts without evidence of migration, aortic rupture, perigraft leaks or dissection.

Aortic aneurysms were obliterated by organized thrombus and aortic ruptures were well healed. The stent grafts were incorporated into the aortic wall. In their upper and lower portions which were in direct contact with the aortic wall; they were smooth and well endothelialized. In the central portions which were in contact with the thrombosed aneurysm, endothelialization was incomplete. Some areas exhibited focal thrombi and some endothelialized areas had an irregular protuberant surface.

Microscopic sections showed replacement of SIS material by dense fibrous tissue forming a neointima well fused with the underlying aortic wall. Foci of chronic inflammation, occasional suture granulomas, localized foreign-body type giant cell reaction to stent wires and small blood vessels were seen within the fibrous tissue. On the luminal surface the neointima over the rupture site and on the upper and lower parts of the stent grafts was covered by intact endothelium. The central portions of the stent graft were only partially endothelialized with residual foci of partially organized thrombus.

Ruptured AAA with its devastating pathophysiological effects carries high mortality, and without treatment is fatal in about 90% of patients. However, even with surgical repair mortality rates are excessively high, averaging about 50% and approaching 90% in patients in shock and patients over 80 years of age. There has been a tendency therefore not to surgically treat patients with significant comorbid factors. With development of new modular and easily customized stent grafts, these patients with high risk factors for surgery might benefit from endoluminal exclusion of ruptured AAA. There have been already 22 patients with ruptured AAA reported in the literature with successful endovascular treatment. To enable basic imaging and stent graft customization, an occlusion balloon is placed from the axillary artery in the distal thoracic descending aorta, as an equivalent of an aortic clamp, in some unstable patients.

The transluminal stent graft placement has great potential in the treatment of aortic rupture, whether it is simple or related to aortic aneurysm. The stent graft mechanically excludes rupture and AAA, the biomaterial SIS used for its cover supports rapid development of neointima consisting of a dense, fibrotic tissue. The neointima adheres to the underlying tissue and the stent graft thus becomes incorporated into the aortic wall.

Development of neointima and its endothelial lining is accelerated in areas where the SIS stent graft cover is in direct contact with the aortic wall. These areas become fully endothelialized at 4 weeks. This is faster than with stent grafts covered with thin-walled polyester (DACRON®) material. At the area of the aneurysm where the SIS cover is in contact with organized thrombus, its development of neointima and particularly of its endothelial lining occurs.

What is claimed is:

1. A stent graft device suitable for placement at a vascular treatment site, the stent graft device comprising:
   a proximal, inflow end of the stent graft device as a whole;
   a distal, outflow end of the stent graft device as a whole;
   a stent frame that includes a plurality of stents connected together with lumens of the respective stents coaligned to form a common continuous lumen extending from a proximal stent frame end to a distal stent frame end, each of said stents having a proximal end and a distal end and including a plurality of struts disposed circumferentially about the stent in a zig-zag pattern, wherein each of the struts in the zig-zag pattern has a proximal end that converges with the proximal end of an adjacent strut at an eyelet occurring at the proximal end of the stent such that the stent provides a circumferential array of proximal eyelets about its proximal end, and wherein each of the struts in the zig-zag pattern further has a distal end that converges with the distal end of an adjacent strut at an eyelet occurring at the distal end of the stent such that the stent provides a circumferential array of distal eyelets about its distal end,
   the plurality of stents including a first stent and an adjacent, second stent connected together by a monofilament that extends through the proximal eyelets of the first stent and the distal eyelets of the second stent, with the proximal eyelets of the first stent and the distal eyelets of the second stent being offset from one another along the monofilament; and
   a covering of collagen having an isolated extracellular matrix layer that becomes remodeled by host tissue, secured to the plurality of stents and extending thereabout between the proximal and distal stent frame ends, wherein the covering is a sleeve that initially has a length about equal to twice the length of the stent frame, a first portion of the sleeve extends along and complements an inside surface of the plurality of stents, and a second portion of the sleeve extends along and complements an outside surface of the plurality of stents, wherein the first portion and the second portion of the sleeve are sutured to the distal stent frame end and the proximal stent frame end of the stent frame, wherein the first portion of the sleeve is secured to the inside surface of the plurality of stents by sutures to struts of the plurality of stents between the distal stent frame end and proximal stent frame end and also by sutures through proximal eyelets and distal eyelets of each of said plurality of stents, wherein the second portion of the sleeve is secured to the outside surface of the plurality of stents by sutures to struts of the plurality of stents between the distal stent frame end and proximal stent frame end and also by sutures through proximal eyelets and distal eyelets of each of said plurality of stents, and the covering extending therealong between the proximal and distal stent frame ends, the stent graft device placeable at the vascular treatment site such that the proximal stent frame end is located upstream of the distal stent frame end, the distal stent frame end providing said distal, outflow end of the stent graft device as a whole through which blood flowing through the stent graft device can exit the stent graft device.

2. The stent graft device of claim 1, wherein the covering is secured to the plurality of stents at locations along the stent frame using a filament of biocompatible material, the locations being adapted to secure the filament in position against movement axially with respect to the stent frame during deployment at a treatment site of a patient.

3. The stent graft device of claim 2, wherein the covering is a sleeve of material.

4. The stent graft device of claim 1, wherein the sleeve is defined by connecting together along a seam, opposite edges of the isolated extracellular matrix layer.

5. A stent graft device comprising:
   a stent frame defining only a single lumen extending from a first end of said stent graft device to a second end of said stent graft device;
   said stent frame having a proximal stent frame end and a distal stent frame end, said stent frame provided by a plurality of stents connected together with lumens of the respective stents coaligned to form a common continuous lumen, each of said stents having a proximal end and a distal end and including a plurality of struts disposed circumferentially about the stent in a zig-zag pattern, wherein each of the struts in the zig-zag pattern has a proximal end that converges with the proximal end of an adjacent strut at an eyelet occurring at the proximal end of the stent such that the stent provides a circumferential array of proximal eyelets about its proximal end, and wherein each of the struts in the zig-zag pattern further has a distal end that converges with the distal end of an adjacent strut at an eyelet occurring at the distal end of the stent such that the stent provides a circumferential array of distal eyelets about its distal end,
   the plurality of stents including a first stent and an adjacent, second stent connected together by a monofilament that extends through the proximal eyelets of the first stent and the distal eyelets of the second stent, with the proximal eyelets of the first stent and the distal eyelets of the second stent being offset from one another along the monofilament;
   the proximal stent frame end providing a proximal, inflow end of the stent graft device as a whole;
   the distal stent frame end providing a distal, outflow end of the stent graft device as a whole;
   a covering of collagen secured to the stent frame, said covering of collagen having an isolated extracellular matrix layer that becomes remodeled by host tissue; and
   wherein the covering is a sleeve having a single lumen therethrough, the sleeve has a length about equal to twice the length of the stent frame, a first portion of the sleeve extends along and complements an inside surface of the stent frame, and a second portion of the sleeve extends along and complements an outside surface of the stent frame, wherein the first portion and the second portion of the sleeve are sutured to the distal stent frame end of the stent frame that provides the distal, outflow end of the stent graft device as a whole, wherein the first portion and the second portion of the sleeve are sutured to the proximal stent frame end of the stent frame that provides the proximal, inflow end of the stent graft device as a whole, wherein the first portion of the sleeve is secured to the inside surface of the stent frame by sutures to struts of the stent frame between the distal stent frame end and proximal stent frame end and also by sutures through proximal eyelets and distal eyelets of each of said plurality of stents, and wherein the second portion of the sleeve is secured to the outside surface of the stent frame by sutures to struts of the stent frame between the distal stent frame end and proximal stent frame end and also by sutures through proximal eyelets and distal eyelets of each of said plurality of stents.

6. The stent graft device of claim 5, wherein the stent frame has eyelets at the proximal and distal ends.

7. The stent graft of claim 6, wherein the covering is sutured to the stent frame using a filament of biocompatible material that extends through the eyelets at the proximal and distal ends of the stent frame.

8. The stent graft device of claim 5, wherein the stent graft device incorporates an absorbable suture material.

9. The stent graft device of claim 5, wherein the covering is secured to the stent frame at locations along the stent frame using a filament of bio compatible material, the locations being adapted to secure the filament in position against movement axially with respect to the stent frame during deployment at a treatment site of a patient.

10. The stent graft device of claim 5, wherein the covering is a sleeve of small intestine submucosa material.

11. The stent graft device of claim 10, wherein the sleeve is defined by connecting together along a seam, opposite edges of at least one flat tissue of the small intestine submucosa material.

* * * * *